US006465434B1

(12) United States Patent
Magnani et al.

(10) Patent No.: US 6,465,434 B1
(45) Date of Patent: Oct. 15, 2002

(54) METHODS AND COMPOSITIONS FOR THE INHIBITION OF CANCER METASTASIS MEDIATED BY ENDOTHELIAL ADHESION MOLECULES

(75) Inventors: John L. Magnani, 8115 Runnymead Dr., Frederick, MD (US) 21702; Eugene C. Butcher, Portola Valley; Ellen L. Berg, Palo Alto, both of CA (US)

(73) Assignees: Stanford University, Palo Alto, CA (US); John L. Magnani, Rockville, MD (US)

( * ) Notice: Subject to any disclaimer, the term of this patent is extended or adjusted under 35 U.S.C. 154(b) by 0 days.

(21) Appl. No.: 09/447,532

(22) Filed: Nov. 23, 1999

Related U.S. Application Data

(63) Continuation of application No. 08/238,684, filed on May 5, 1994, now Pat. No. 6,121,233, which is a continuation of application No. 07/721,771, filed on Jun. 25, 1991, now abandoned, which is a continuation-in-part of application No. 07/688,037, filed on Apr. 19, 1991, now abandoned.

(51) Int. Cl.$^7$ .............................................. A01N 43/04

(52) U.S. Cl. ............................. 514/23; 514/53; 514/54; 514/61

(58) Field of Search ............................. 514/23, 53, 54, 514/61

(56) References Cited

U.S. PATENT DOCUMENTS

| 4,471,057 A | | 9/1984 | Koprowski et al. |
| 4,851,511 A | | 7/1989 | Hakomori et al. |
| 4,859,769 A | | 8/1989 | Karlsson et al. |
| 4,876,199 A | | 10/1989 | Hakomori |
| 4,946,830 A | * | 8/1990 | Pulverer et al. |
| 5,143,712 A | | 9/1992 | Brandley et al. |
| 5,211,937 A | | 5/1993 | Brandley et al. |
| 5,723,583 A | | 3/1998 | Seed et al. |

FOREIGN PATENT DOCUMENTS

| EP | 381 310 A1 | 8/1990 |
| EP | 408 859 A2 | 1/1991 |
| WO | WO 90/13300 | 11/1990 |
| WO | WO 91/19502 | 12/1991 |
| WO | WO 92/01718 | 2/1992 |
| WO | WO 92/07572 | 5/1992 |

OTHER PUBLICATIONS

Baeckström et al., "Purification and Characterization of a Membrane–bound and a Secreted Mucin–type Glycoprotein Carrying the Carcinoma–associated Sialyl–Le$^a$ Epitope on Distinct Core Proteins," *J. Biol. Chem.* 266(32):21537–21547, 1991.

Berg et al., "A Carbohydrate Domain Common to Both Sialyl Le$^a$ and Sialyl Le$^x$ Is Recognized by the Endothelial Cell Leukocyte Adhesion Molecule ELAM–1," *J. Biol. Chem.* 266(23):14869–14872, 1991.

Berg et al., "The Cutaneous Lymphocyte Antigen Is a Skin Lymphocyte Homing Receptor for the Vascular Lectin Endothelial Cell–Leukocyte Adhesion Molecule 1," *J. Exp. Med.* 174:1461–1466, 1991.

Bird and Kimber, "Oligosaccharides Containing Fucose Linked $\alpha(1$–$3)$ and $\alpha(1$–$4)$ to N–Acetylglucosamine Cause Decompaction of Mouse Morulae," *Devel. Biol.* 104:449–460, 1984.

Bowen et al., "Characterization of a Human Homologue of the Murine Peripheral Lymph Node Homing Receptor," *Journal of Cell Biology* 109:421–427, 1989.

Brandley et al., "Carbohydrate Ligands of LEC Cell Adhesion Molecules," *Cell* 63:861–863, 1990.

Broquet et al. "Effect of Desipramine on a Glycoprotein Sialyltransferase Activity in C6 Cultured Glioma Cells," *J. Neurochem.* 54:388–394, 1990.

Childs et al., "High–molecular–weight glycoproteins are the major carriers of the carbohydrate differentiation antigens I, i and SSEA–1 of mouse teratocarcinoma cells," *Biochem. J.* 215:491–503, 1983.

Ching and Rhodes, "Purification and Characterization of a Peanut–Agglutinin–Binding Pancreatic–Cancer–Related Serum Mucus Glycoprotein," *Int. J. Cancer* 45:1022–1027, 1990.

Corral et al., "Requirements for Sialic Acid on Neutrophils in a GMP–140 (PADGEM) Mediated Adhesive Interaction with Activated Platelets," *Biochem. Biophys. Res. Commun.* 172:1349–1356, 1990.

Duijvestijn et al., "High Endothelial Differentiation in Human Lymphoid and Inflammatory Tissues Defined by Monoclonal Antibody HECA–452," *Am. J. Path.* 130:147–155, 1988.

Edgington, "How Sweet It Is: Selectin–Mediating Drugs," *Biotechnology* 10:383–389, 1992.

(List continued on next page.)

Primary Examiner—Sheela Huff
(74) Attorney, Agent, or Firm—SEED Intellectual Property Law Group PLLC

(57) ABSTRACT

Methods and compositions are disclosed for the inhibition of cancer metastases mediated by endothelial adhesion molecules. The present invention discloses that sialyl Le$^a$ and di-sialyl Le$^a$, which are expressed at the surface of cancer cells, function as a binding partner for LEC-CAMs, such as ELAM-1, which are expressed at the surface of endothelial cells. The present invention also discloses that LEC-CAMs, such as ELAM-1, involved in cancer metastasis share a carbohydrate domain common to both sialyl Le$^a$ and sialyl Le$^x$. Antibodies, saccharides, glycoconjugates, enzyme inhibitors and other compounds may be used in the methods of the present invention to inhibit the binding of malignant cells to endothelial cells for a variety of purposes in vivo and in vitro.

4 Claims, 3 Drawing Sheets

OTHER PUBLICATIONS

Eggens et al., "A Role of Carbohydrate–Carbohydrate Interaction in the Process of Specific Cell Recognition During Embryogenesis and Organogenesis: A Preliminary Note," *Biochem. Biophys. Res. Commun.* 158(3):913–920, 1989.

Eggens et al., "Specific Interaction between $Le^x$ and $Le^x$ Determinants. A Possible Basis for Cell Recognition in Preimplantation Embryos and in Embryonal Carcinona Cells," *J. Biol. Chem.* 246(16):9476–9484, 1989.

Fenderson et al., "A Multivalent Lacto–N–Fucopenataose III–Lysyllysine Conjugate Decompacts Preimplantation Mouse Embryos, While the Free Oligosaccharide is Ineffective," *J. Exp. Med.* 160:1591–1596, 1984.

Fenderson et al., "Coordinate Expression of X and Y Haptens during Murine Embryogenesis," *Devel. Biol.* 114:12–21, 1986.

Fenderson et al., "The blood group I antigen defined by monoclonal antibody C6 is a marker of early mesoderm during murine embryogenesis," *Differentiation* 38:124–133, 1988.

Fukushi et al., "Novel Fucolipids Accumulating in Human Adenocarcinoma. II. Selective Isolation of Hybridoma Antibodies That Differentially Recognize Mono–, Di–, and Trifucosylated Type 2 Chain," *J. Biol. Chem.* 259(7):4681–4685, 1984.

Fukushi et al., "Novel Fucolipids Accumulating in Human Adenocarcinoma. III. A Hybridoma Antibody (FH6) Defining a Human Cancer–Associated Difucoganglioside ($VI^3NeuAcV^3III^3Fuc_2nLc_6$)," *J. Biol. Chem.* 259(16):10511–10517, 1984.

Gabius et al., "Endogenous Tumor Lectins: Overview and Perspectives," *Anticancer Res.* 6:573–578, 1986.

Gallatin et al., "A cell–surface molecule involved in organ-specific homing of lymphocyctes," *Nature* 304:30–34, 1983.

Gooi et al., "Stage–specific embryonic antigen involves α 1 → 'fucosylated type 2 blood group chains," *Nature* 292:156–158, 1981.

Hakomori et al., "Novel Fucolipids Accumulating in Human Adenocarcinoma. I. Glycolipids With Di– or Trifucosylated Type 2 Chain," *J. Biol. Chem.* 259(7):4672–4680, 1984.

Hakamori et al., "The Hapten Structure of a Developmentally Regulated Glycolipid Antigen (SSEA–1) Isolated From Human Erythrocytes and Adenocarcinoma: A Preliminary Note," *Biochem. Biophys. Res. Comm.* 100(4):1578–1586, 1981.

Hakomori S., "Aberrant Glycosylation in Cancer Cell Membranes as Focused on Glycolipids: Overew and Perspectives," *Cancer Res.* 45:2405–2414, 1985.

Handa et al., "Selectin GMP–140 (CD62; PADGEM) Binds to Sialosyl –$Le^a$ and Sialosyl–$Le^x$, and Sulfated Glycans Modulate this Binding," *Biochemical and Biophysical Research Communication* 181(3):1223–1230, 1991.

Hansson and Zopf, "Biosynthesis of the Cancer–associated Sialyl–$Le^a$ Antigen," *Journal of Biological Chemistry* 260(16):9388–9392, 1985.

Holmes et al., "Enzymatic Basis for the Accumulation of Glycolipids with X and Dimeric X Determinants in Human Lung Cancer Cells (NCI–H69)," *J. Biol. Chem.* 260(12):7619–7627, 1985.

Huse et al., "Generation of a Large Combinatorial Library of the Immunoglobulin Repertoire in Phage Lambda," *Science* 246:1275–1281, 1989.

Hynes, R., "Integrins: A Family of Cell Surface Receptors," *Cell* 48:549–554, 1987.

Issekutz, T., "Inhibition of in Vivo Lymphoctye Migration of Inflammation and Homing to Lymphoid Tissues by the TA–2 Monoclonal Antibody. A Likely Role for VLA–4 in Vivo," *Journal of Immunology* 147:4178–4184, 1991.

Jeffrey et al., "Affinity Chromatography of Carbohydrate–Specific Immunoglobulins: Coupling of Oligosaccharides to Sepharose ," *Biochem. Biophys. Res. Commun.* 62:608–613, 1975.

Kannagi et al., "New Globoseries Glycosphingolipids in Human Teratocarcinoma Reactive with the Monoclonal Antibody Directed to a Developmentally Regualted Antigen, Stage–specific Embryonic Antigen 3," *J. Biol. Chem.* 258(14):8934–8942, 1983.

Kannagi et al., "Stage–specific embryonic antigens (SSEA–3 and –4) are epitopes of a unique globo–series ganglioside isolated from human teratocarcinoma cells," *Embo J.* 2(12):2355–2361, 1983.

Karaivanova et al., "Partial Characterization of Microsomal Sialyltransferase From Chicken Liver and Hepatoma Mc–29: II. Measurement of Enzymer Activities Utilizing Microsomal Glycoproteins as Exogenous Acceptors," *Cancer Biochem. Biophys.* 11:311–315, 1990.

Kitagawa et al., "Characterization of Mucin–Type Oligosaccharides With the Sialyl–$Le^a$ Structure From Human Colorectal Adenocarcinoma Cells," *Biochem. Biophys. Res. Commun.* 178(3):1429–1436, 1991.

Kitagawa et al., "Immunoaffinity Isolation of a Sialyl–$Le^a$ Oligosaccharide from Human Milk," *J. Biochem.* 104:591–594, 1988.

Köhler and Milstein, "Continuous cultures of fused cells secreting antibody of predefined specificity," *Nature* 256:495–497, 1975.

Köhler and Milstein, "Derivation of specific antibody–producing tissue culture and tumor lines by cell fusion," *Eur. J. Immunol.* 6:511–519, 1976.

Kojima and Hakomori, "Specific Interaction between Gngliotriaosylceramide ($G_{g3}$) and Sialosyllactosylceramide ($G_{M3}$) as a Basis for Specific Cellular Recognition between Lymphoma and Melanoma Cells," *J. Biol. Chem.* 264(34):20159–20162, 1989.

Koprowski et al., "Colorectal Carcinoma Antigens Detected by Hybridoma Antibodies," *Somatic Cell Genetics* 5(6):957–972, 1979.

Kuzuoka, "Antitumor activity of murine monoclonal antibody NCC–ST–421," *Chem. Ab.* 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→•) Structural Element Revealed By 500–Mhz H NMR Spectroscopy," *Journal of Biological Chemistry* 259(14):9051–9058, 1984.

Larsen et al., PADGEM–Dependent Adhesion of Platelets to Monocytes and Neutrophils Is Mediated by a Lineage–Specific Carbohydrate, LNF III (CD15), *Cell* 63:467–474, 1990.

Lindenberg et al., "Carbohydrate binding properties of mouse embryos," *J. Reprod. Fert.* 89:431–439, 1990.

Lipartiti et al., "Monosialoganglioside GM1 Reduces NMDA Neurotoxicity in Neonatal Rat Brain," *Experimental Neurology* 113:301–305, 1991.

Lowe et al., "A transfected human fucosyltransferase cDNA determines biosynthesis of oligosaccharide ligand(s) for endothelial–leukocyte adhesion molecule I," *Biochem. Soc. Trans.* 19(3):649–653, 1991.

Lowe et al., "ELAM–1–Dependent Cell Adhesion to Vascular Endothelium Determined by a Transfected Human Fucosyltransferase cDNA," *Cell* 63:475–484, 1990.

Macher et al., "A Novel Carbohydrate, Differentiation Antigen on Fucogangliosides of Human Myeloid Cells Recognized by Monoclonal Antibody VIM–2," *Journal of Biological Chemistry* 263(21):10186–10191, 1988.

Magnani et al., "Identification of the Gastrointestinal and Pancreatic Cancer–associated Antigen Detected by Monoclonal Antibody 19–9 in the Sera of Patients as a Mucin," *Cancer Res.* 43:5489–5492, 1983.

Magnani et al., "A Monoclonal Antibody–defined Antigen Associated with Gastrointestinal Cancer Is a Ganglioside Containing Sialylated Lacto–N–fucopentaose II," *Journal of Biological Chemistry* 257(23):14365–14369, 1982.

Magnani, J., "Carbohydrate Sequences Detected By Murine Monoclonal Antibodies," *Chemistry and Physics of Lipids* 42:65–74, 1986.

Mulligan and Berg, "Selection for animal cells that express the *Escherichia coli* gene coding for xanthine–gunine phosphoribosyltransferase," *Proc. Natl. Acad. Sci. USA* 78:2072–2076, 1981.

Nicolaou et al., "Total Synthesis of the Tumor–Associated $Le^x$ Family of Glycosphingolipids," *J. Amer. Chem. Soc.* 112:3693–3695, 1990.

Nudelman et al., "Novel Fucolipids of Human Adenocarcinoma: Disialosyl $Le^a$ Antigen ($III^4FucIII^6NeuAcIV^3NeuAcLc_4$) of Human Colonic Adenocarcinoma and the Monoclonal Antibody (FH7) Defining This Structure," *J. Biol. Chem.* 261:5487–5495, 1986.

Palcic et al., "Enzymic Synthesis of Oligosaccharides Terminating in the Tumor–Associated Sialyl–Lewis–a Determinant," *Carbohydr. Res.* 190:1–11, 1989.

Palcic et al., "Regulation of N–Acetylglucosaminyltransferase V Activity. Kinetic Comparisons of Parental Rous Sarcoma Virus–Transformed BHK, and L–Phytohemagglutnin–Resistant BHK Cells Using Synthetic Substrates and an Inhibitory Substrated Analog," *J. Biol. Chem.* 265:6759–6769, 1990.

Palcic et al., A Bisubstrate Analog Inhibitor for $\alpha(1\rightarrow 2)$–Fucosyltransferase, *J. Biol. Chem.* 264:17174–17181, 1989.

Phillips et al., "ELAM–1 Mediates Cell Adhesion by Recognition of a Carbohydrate Ligand, Sialyl–$Le^x$," *Science* 250:1130–1132, 1990.

Picker et al., "The Neutrophil Selectin LECAM–1 Presents Carbohydrate Ligands to the Vascular Selectins ELAM–1 and GMP–140," *Cell* 66:921–933, 1991.

Prokazova et al., "Sialylated lactosylceramides. Possible inducers of non–specific immunosuppression and atherosclerotic lesions," *European Journal of Biochemistry* 172:1–6, 1988.

Rauvala et al., "Studies on Cell Adhesion and Recognition. I. Extent and Specificity of Cell Adhesion Triggered by Carbohydrate–reactive Proteins (Glycosidases and Lectins) and by Fibronectin," *J. Cell Biol.* 88:127–137, 1981.

Rice and Bevilacqua, "An Inducible Endothelial Cell Surface Glycoprotein Mediates Melanoma Adhesion," *Science* 246:1303–1306, 1989.

Ruoslahti and Pierschbacher, "New Perspectives in Cell Adhesion: RGD and Integrins," *Science* 238:491–497, 1987.

Sakurai et al., "Selection of a Monoclonal Antibody Reactive with a High–Molecular–Weight Glycoprotein Circulating in the Body Fluid of Gastrointestinal Cancer Patients," *Cancer Research* 48:4053–4058, 1988.

Sastry et al., "Cloning of the immunological repertoire in *Escherichia coli* for generation of monoclonal catalytic antibodies: Construction of a heavy chain variable region–specific cDNA library," *Proc. Natl. Acad. Sci. USA* 86:5728–5732, 1989.

Shitara et al., "Application of Anti–Sialyl $Le^a$ Monoclonal antibody, KM231, for Immunotherapy of Cancer," *Anticancer Res.* 11:2003–2014, 1991.

Stanley and Atkinson, "The LEC11 Chinese Hamster Ovary Mutant Synthesizes N–Linked Carbohydrates Containing Sialylated, Fucosylated Lactosamine Units. Analysis By One–and Two–Dimensional H NMR Spectroscopy," *J. Biol. Chem.* 263(23):11374–11381, 1988.

Stephens and Cockett, "The construction of highly efficient and versatile set of mammalian expression vectors," *Nucleic Acids Research.* 17:7110, 1989.

Streeter et al., "Immunohistologic and Functional Characterization of a Vascular Addressin Involved in Lymphocyte Homing into Peripheral Lymph Nodes," *Journal of Cell Biology* 107: 1853–1862, 1988.

Stroud et al., "Extended Type 1 Chain Glycosphingolipids: Dimeric $Le^a$ ($III^4V^4Fuc_2Lc_6$) as Human Tumor–associated Antigen," *J. Biol. Chem.* 266(13):8439–8446, 1991.

Svenson and Lindberg, "Coupling of Acid Labile Salmonella Specific Oligosaccharides to Macromolecular Carriers," *J. Immunol. Meth.* 25:323–335, 1979.

Takada et al., "Adhesion of Human Cancer Cells to Vascular Endothelium Mediated by a Carbohydrate Antigen, Sialyl Lewis $A^1$," *Biochem. Biophys. Res. Commun.* 179(2):713–719, 1991.

Takeichi, M., "Cadherins: a molecular family essential for selective cell–cell adhesion and animal morphogenesis," *Trends Genet.* 3(8):213–217, 1987.

Trouet et al., "A covalent linkage between daunorubicin and proteins that is stable in serum and reversible by lysosomal hydrolases, as required for a lysosomotropic drug–carrier conjugate: In vitro and in vivo studies," *Proc. Natl. Acad. Sci. USA* 79:626–629, 1982.

Tyrrell et al., "Structural requirements for the carbohydrate ligand of E–selectin," *Proc. Natl. Acad. Sci. USA* 88:10372–10376, 1991.

Walz et al., "Recognition by ELAM–1 of the Sialyl–$Le^x$ Determinant on Myeloid and Tumor Cells," *Science* 250:1132–1135, 1190.

Ward and Mulligan, "Blocking of adhesion molecules in vivo as anti–inflammatory therapy", *Immunology* 1: 165–171, 1994.

Whisler and Yates, "Regulation of Lymphocyte Responses By Human Gangliosides. I. Characteristics of Inhibitory Effects and the Induction of Impaired Activation," *Journal of Immunology* 125(5):2106–2111, 1980.

Zhou et al., "The Selectin GMP–140 Binds to Sialylated, Fucosylated Lactosaminoglycans on Both Myeloid and Nonmyeloid Cells," *Journal of Cell Biology* 115(2):557–564, 1991.

Zopf et al., "Affinity Purification of Antibodies Using Oligosaccharide–Phenethylamine Derivatives Coupled to Sepharose," *Meth. Enzymol.* 50:171–175, 1978.

\* cited by examiner

METHODS AND COMPOSITIONS FOR THE INHIBITION OF CANCER METASTASIS MEDIATED BY ENDOTHELIAL ADHESION MOLECULES

CROSS-REFERENCE TO RELATED APPLICATIONS

This application is a continuation of U.S. patent application Ser. No. 08/238,684, filed May 5, 1994, now U.S. Pat. No. 6,121,233; which application is a continuation of U.S. patent application Ser. No. 07/721,771, filed Jun. 25, 1991, abandoned; which application is a continuation-in-part of U.S. patent application Ser. No. 07/688,037, filed Apr. 19, 1991, abandoned.

TECHNICAL FIELD

The present invention is generally directed toward the inhibition of cancer metastasis mediated by endothelial adhesion molecules, and more specifically, toward such inhibition through the use of saccharides, glycoconjugates, antibodies, enzyme inhibitors, and other agents which disrupt such binding of cancer cells to endothelia.

BACKGROUND OF THE INVENTION

Despite enormous investments of financial and human resources, cancer remains one of the major causes of death. Current cancer therapies cure only about fifty percent of the patients who develop a malignant tumor. In most human malignancies, metastasis is the major cause of death.

Metastasis is the formation of a secondary tumor colony at a distant site. It is a multistep process of which tumor invasion is an early event. Tumor cells locally invade host tissue barriers, such as the epithelial basement membrane, to reach the interstitial stroma, where they gain access to blood vessels ("hematogenous metastasis") or lymphatic channels for further dissemination. After invading the endothelial layer of a vessel wall, the circulating tumor cells are dislodged into the circulation and arrest in the precapillary venules of the target organ by adherence to endothelial cell lumenal surfaces, or exposed basement membranes. The tumor cells again invade the vascular wall to enter the organ parenchyma. Finally, the extravasated tumor cell grows in a tissue different from where it originated.

Most cancer cells fail to survive in the circulation and it appears that normally the lining of blood vessels acts as a barrier to tumor cell extravasation. Endothelial injury or perturbation increases tumor metastasis. In addition, certain factors, such as cytokines, have been shown to substantially increase the adhesion of cancer cells to treated endothelium in vitro. Interleukin 1 (IL-1) and tumor necrosis factor (TNF), which are cytokines, each stimulate the biosynthesis and expression of a cell surface receptor called ELAM-1 (endothelial leukocyte adhesion molecule). ELAM-1 is a member of a family of calcium-dependent cell adhesion receptors, known as LEC-CAMs or selecting, which includes LECAM-1 and GMP-140 (also known as PADGEM or CD62). During an inflammatory response, ELAM-1 on endothelial cells functions as a "homing receptor" for leukocytes. Recently, ELAM-1 on endothelial cells was shown to mediate the increased adhesion of colon cancer cells to endothelium treated with cytokines (Rice and Bevilacqua, *Science* 246:1303–1306, 1989).

In most human malignancies, distant metastases are often too small to be detected at the time the primary tumor is treated. Furthermore, widespread initiation of metastatic colonies usually occurs before clinical symptoms of metastatic disease are evident. The size and age variation in metastases, their dispersed anatomical location, and their heterogeneous composition are all factors that hinder surgical removal and limit the concentration of anticancer drugs that can be delivered to the metastatic colonies. It has been estimated, for example, that in 1991 there will be over 60,000 deaths and over 150,000 new cases from just colorectal cancer in the U.S. alone.

Due to the difficulties in the current approaches to the treatment and prevention of metastases, there is a need in the art for improved methods and compositions for inhibiting metastasis mediated by endothelial adhesion molecules. The present invention fills this need, and further provides other related advantages.

SUMMARY OF THE INVENTION

Briefly stated, the present invention provides methods and compositions for the inhibition of cancer metastasis mediated by endothelial adhesion molecules. In one aspect, the present invention provides methods for inhibiting, within a biological preparation, the binding of malignant cells expressing sialyl $Le^a$ or di-sialyl $Le^a$, to endothelial cells. In one embodiment, the method comprises incubating the biological preparation with at least one agent that inhibits the binding of malignant cells expressing sialyl $Le^a$ or di-sialyl $Le^a$, to endothelial cells expressing a LEC-CAM. In another embodiment, the method comprises incubating the biological preparation with at least one agent that inhibits the binding of malignant cells expressing sialyl $Le^a$ or di-sialyl $Le^a$, to endothelial cells expressing ELAM-1. In another embodiment, the method comprises incubating the malignant cells with at least one enzyme inhibitor that inhibits the biosynthesis of sialyl $Le^a$ or di-sialyl $Le^a$ by the malignant cells.

In another aspect of the present invention, methods are provided for inhibiting the spread of malignant cells expressing sialyl $Le^a$ or di-sialyl $Le^a$, to secondary sites in a warm-blooded animal. In one embodiment, the method comprises administering to a warm-blooded animal an effective amount of at least one agent that inhibits the binding of malignant cells expressing sialyl $Le^a$ or di-sialyl $Le^a$, to endothelial cells expressing a LEC-CAM. In another embodiment involving hematogenous metastasis, the method comprises administering to a warm-blooded animal an effective amount of at least one agent that inhibits the binding of malignant cells expressing sialyl $Le^a$ or di-sialyl $Le^a$, to endothelial cells expressing ELAM-1. In another embodiment, the method comprises administering to a warm-blooded animal an effective amount of at least one enzyme inhibitor that inhibits the biosynthesis of sialyl $Le^a$ or di-sialyl $Le^a$ by the malignant cells.

In a related aspect, methods are provided for inhibiting within a biological preparation the binding of malignant cells expressing sialyl $Le^a$, di-sialyl $Le^a$ or sialyl $Le^x$, to endothelial cells. In one embodiment, the method comprises incubating a biological preparation, containing endothelial cells expressing a LEC-CAM, with at least one agent capable of reacting with both sialyl $Le^a$ and sialyl $Le^x$. In another embodiment, the method comprises incubating a biological preparation, containing endothelial cells expressing ELAM-1, with at least one agent capable of reacting with both sialyl $Le^a$ and sialyl $Le^x$.

In another related aspect, methods are provided for inhibiting the spread of malignant cells expressing sialyl $Le^a$, di-sialyl $Le^a$ or dialyl $Le^x$, to secondary sites in a warm-blooded aminal. In one embodiment, the method comprises administering to a warm-blooded animal an effective amount of at least one agent capable of reacting with both sialyl Le$^a$ and sialyl Le$^x$. In another embodiment involving hematogenous metastasis, the method comprises administering to a warm-blooded animal an effective amount of at least one agent capable of reacting with both sialyl Le$^a$ and sialyl Le$^x$.

These and other aspects of the present invention will become evident upon reference to the following detailed description and attached drawings.

DETAILED DESCRIPTION OF THE INVENTION

Figure 1:
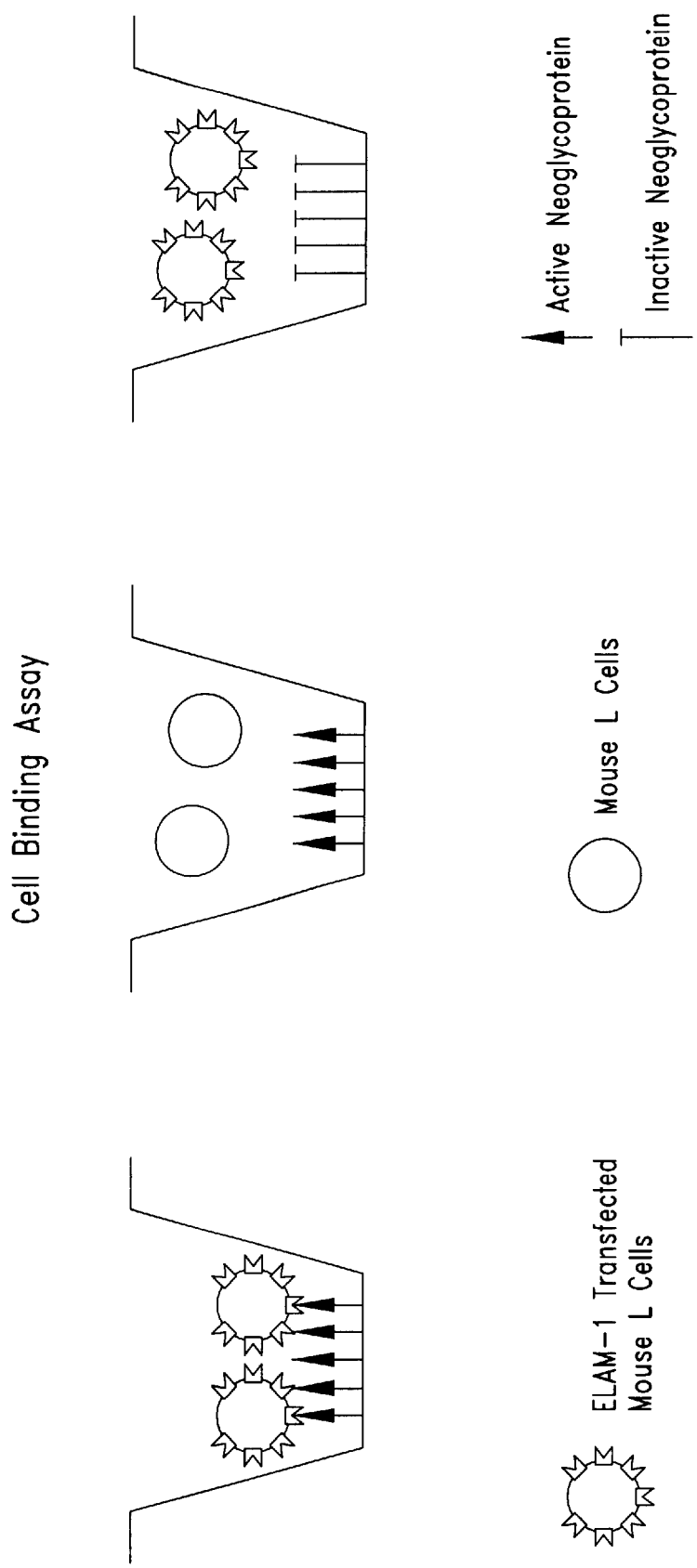
FIG. 1 describes pictorially a cell binding assay used to assess binding of ELAM-1 transfected cells to neoglycoproteins.
Figure 2:
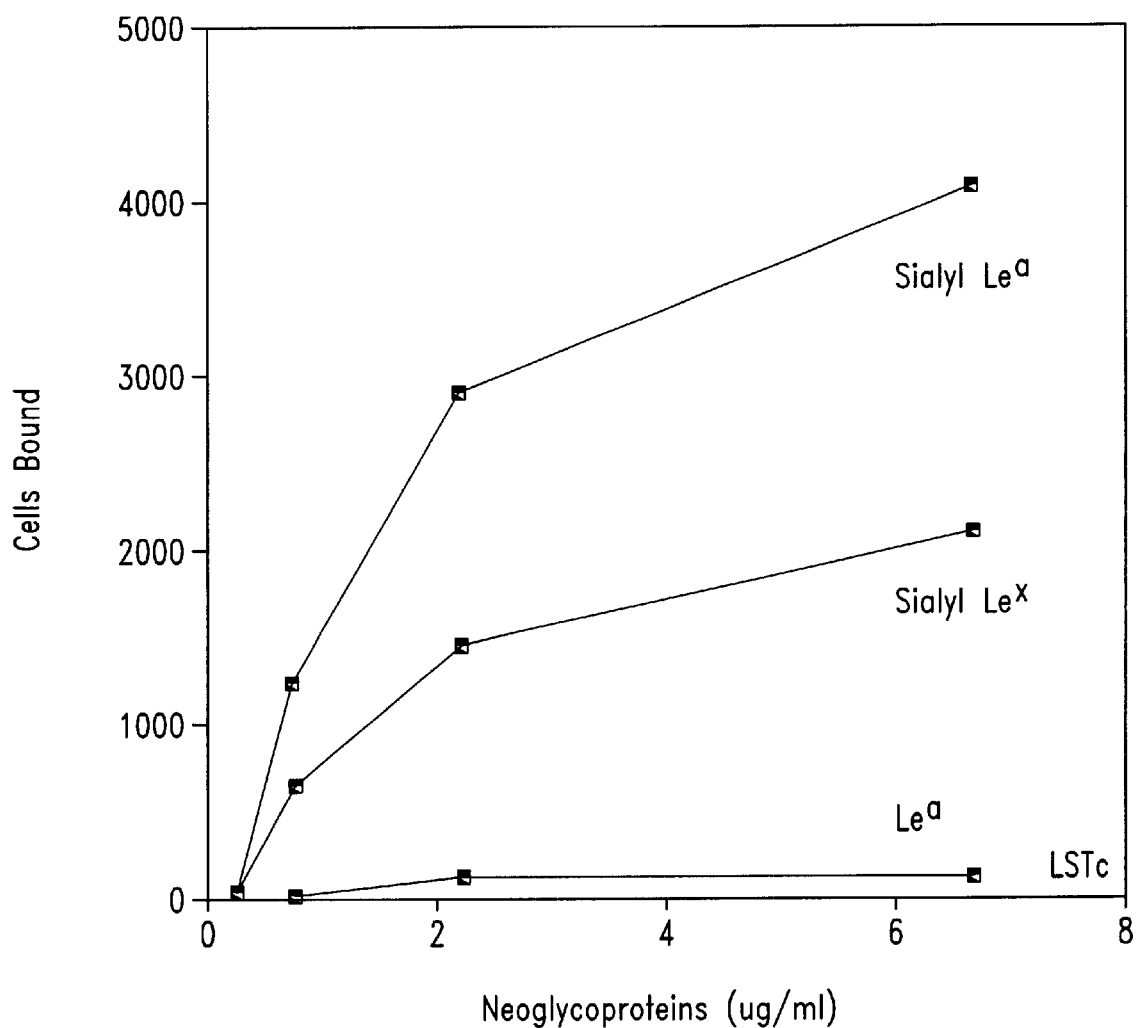
FIG. 2 graphically illustrates the relative binding of ELAM-1 transfected cells to certain neoglycoproteins.
Figure 3:
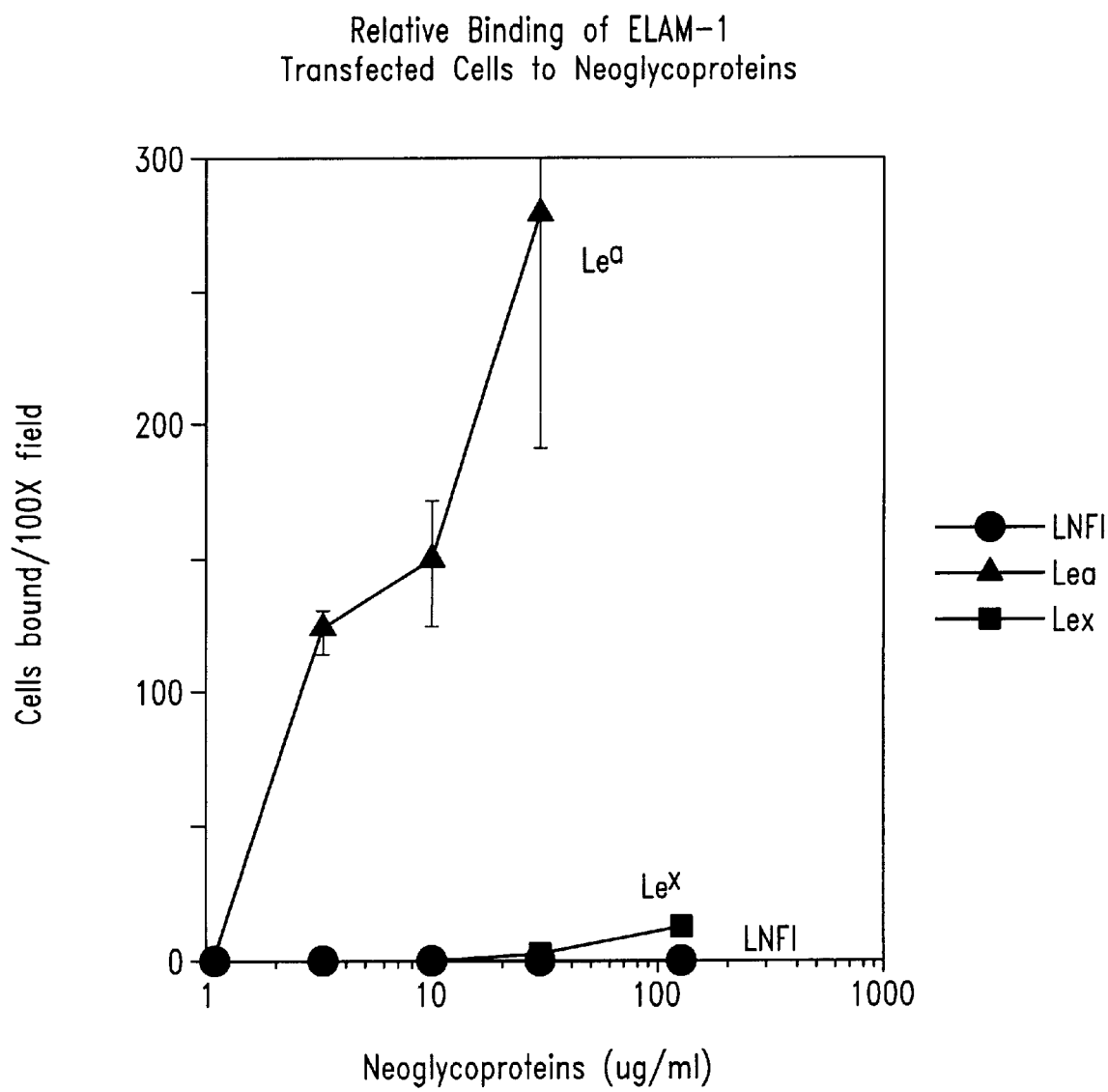
FIG. 3 graphically illustrates the relative binding of ELAM-1 transfected cells to certain neoglycoproteins.

Prior to setting forth the invention, it may be helpful to an understanding thereof to set forth definitions of certain terms to be used hereinafter.

Antibody—as used herein, includes both monoclonal and polyclonal antibodies and may be an intact molecule, a fragment thereof, or a functional equivalent thereof. The antibody may be genetically engineered. Examples of antibody fragments include F(ab')$_2$, Fab', Fab and Fv.

Saccharide—as used herein, includes oligosaccharides, and may be naturally derived, synthetically prepared, portions of either, and derivatives of any of the foregoing.

Glycoconiugate—as used herein, includes a saccharide which is coupled to a non-saccharide molecule, e.g., a lipid or a polypeptide.

As noted above, the present invention is generally directed towards methods and compositions for the inhibition of cancer metastasis mediated by endothelial adhesion molecules. More specifically, the disclosure of the present invention shows that antibodies, saccharides, glycoconjugates therefrom or enzyme inhibitors may be used to inhibit the binding of malignant cells to endothelial cells for a variety of purposes in vivo and in vitro.

As described above, metastasis is a multistep process. During metastasis, cancer cells circulate through the microvascular and lymph systems and then migrate through the walls of the blood or lymph vessels to establish a new and aggressive tumor at a secondary organ site. A critical step in the metastasis process is the adherence of circulating cancer cells to the endothelial lining of blood vessel or lymph vessel walls. As disclosed within the present invention, the carbohydrates sialyl Le$^a$ and di-sialyl Le$^a$, which are expressed at the surface of certain cancer cells, function as a ligand (i.e., binding partner) for LEC-CAMs, such as ELAM-1, which are expressed at the surface of endothelial cells. Therefore, for those cancer cells, metastasis involves the adherence of cancer cells to the endothelial cells via the binding of sialyl Le$^a$ and/or di-sialyl Le$^a$ on the cancer cells to adhesion molecules on endothelial cells. Other cancer cells express predominantly sialyl Le$^x$, or sialyl Le$^x$ and sialyl Le$^a$ (and/or di-sialyl Le$^a$). The present invention discloses that LEC-CAMs, such as ELAM-1, share a carbohydrate domain common to both sialyl Le$^a$ and sialyl Le$^x$ on malignant cells, and therefore agents can be produced which are capable of binding to both. Inhibition of the initial binding event between LEC-CAMs and sialylated structures by the methods of the present invention prevents the adhesion of metastatic cells to the endothelial lining of blood or lymph vessel walls, thereby eliminating the spread of metastatic cells to secondary organs. Suitable blocking agents include those which inhibit the binding of malignant cells expressing sialyl Le$^a$, di-sialyl Le$^a$, or sialyl Le$^x$, to endothelial cells expressing LEC-CAM adhesion molecules such as ELAM-1. Representative agents include antibodies, saccharides and glycoconjugates therefrom.

The antibodies employed in the present invention may be polyclonal or monoclonal antibodies. Briefly, polyclonal antibodies may be produced by immunization of an animal and subsequent collection of its sera. Immunization is accomplished, for example, by a systemic administration, such as by subcutaneous, intrasplenic or intramuscular injection, into a rabbit, rat or mouse. It is generally preferred to follow the initial immunization with one or more booster immunizations prior to sera collection. Such methodology is well known and described in a number of references.

Monoclonal antibodies (MAbs) suitable within the present invention include those of murine or human origin, or chimeric antibodies such as those which combine portions of both human and murine antibodies (i.e., antigen binding region of murine antibody plus constant regions of human antibody). Human and chimeric antibodies may be produced using methods known by those skilled in the art. Human antibodies and chimeric human-mouse antibodies are advantageous because they are less likely than murine antibodies to cause the production of anti-antibodies when administered clinically.

MAbs may be generally produced by the method of Kohler and Milstein (*Nature* 256:495–497, 1975; *Eur. J. Immunol.* 6:511–519, 1976). Briefly, the lymph nodes and/or spleens of an animal immunized with sialyl Le$^a$ or di-sialyl Le$^a$ are fused with myeloma cells to form hybrid cell lines ("hybridomas" or "clones"). Each hybridoma secretes a single type of immunoglobulin and, like the myeloma cells, has the potential for indefinite cell division. It may be desirable to couple such molecules to a carrier to increase their immunogenicity. Suitable carriers include keyhole limpet hemocyanin, thyroglobulin, bovine serum albumin and derivatives thereof. An alternative to the production of MAbs via hybridomas is the creation of MAb expression libraries using bacteriophage and bacteria (e.g., Sastry et al., *Proc. Natl. Acad. Sci USA* 86:5728, 1989; Huse et al., *Science* 246:1275, 1989). Selection of antibodies exhibiting appropriate specificity may be performed in a variety of ways which will be evident to those skilled in the art. Typically, such antibodies will selectively bind with an affinity of about $10^7$ liters/mol or higher.

Representative examples of MAbs suitable within the present invention include N-19-9 and HECA-452 for sialyl Le$^a$, and FH-7 for di-sialyl Le$^a$. MAb N-19-9 is available from ATCC (American Type Tissue Collection, Rockville, Maryland) as ATCC HB 8059 or may be produced as described in U.S. Pat. No. 4,471,057 (and *Somatic Cell Genet.* 5:957–971, 1979; *J. Biol. Chem.* 257:14365, 1982). MAb HECA-452 may be produced according to Duijvestijn et al., *Am. J. Path.* 130:147–155, 1988. FH-7 may be produced according to Nudelman et al., *J. Biol. Chem.* 261:5487, 1986.

In addition to antibodies which are capable of binding to sialyl Le$^a$, di-sialyl Le$^a$ or sialyl Le$^x$, saccharides and glycoconjugates therefrom may also inhibit the binding of metastatic cells expressing sialyl Le$^a$, di-sialyl Le$^a$ or sialyl Le$^x$, to endothelia. As used herein, the terms "sialyl Le$^a$" and "di-sialyl Le$^a$" represent structures I and II, respectively, as follows:

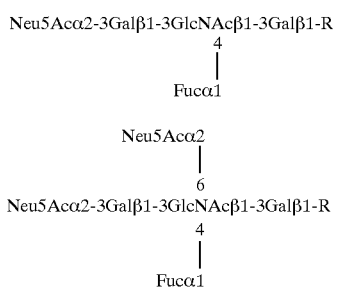

$$\text{Neu5Ac}\alpha\text{2-3Gal}\beta\text{1-3GlcNAc}\beta\text{1-3Gal}\beta\text{1-R} \quad (I)$$
$$\underset{|}{\overset{4}{\phantom{X}}}$$
$$\text{Fuc}\alpha\text{1}$$

$$\text{Neu5Ac}\alpha\text{2} \quad (II)$$
$$\underset{6}{\overset{|}{\phantom{X}}}$$
$$\text{Neu5Ac}\alpha\text{2-3Gal}\beta\text{1-3GlcNAc}\beta\text{1-3Gal}\beta\text{1-R}$$
$$\underset{|}{\overset{4}{\phantom{X}}}$$
$$\text{Fuc}\alpha\text{1}$$

Neu5Ac represents sialic acid; Gal represents galactose; GlcNAc represents N-acetyl-glucosamine; Fuc represents fucose and R is typically a ceramide (with a glucose residue interposed) or a protein. Sialyl Le$^x$ is an isomer of sialyl Le$^a$ wherein the Gal-GlcNAc linkage is β1-4 and the Fuc-GlcNAc linkage is α1→3. Saccharides suitable within the present invention include the carbohydrate portion of sialyl Le$^a$ or di-sialyl Le$^a$ (i.e., formula I or II minus R), and derivatives of either, including those which cross-react with both sialyl Le$^a$ and sialyl Le$^x$. Derivatives of these compounds include substitution of individual saccharide residues with other saccharide residues and/or with non-saccharide molecules such as hexyl rings without hydroxyl groups. For example, the internal GlcNAc may be replaced with another saccharide residue such as a glucose (Glc). Alternatively (or in addition to substitutions), the carbohydrate portion of sialyl Le$^a$, di-sialyl Le$^a$, or derivatives thereof, may be truncated by deletion of one or more saccharide residues. For example, a tetrasaccharide may be created with the structure:

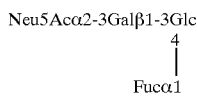

$$\text{Neu5Ac}\alpha\text{2-3Gal}\beta\text{1-3Glc}$$
$$\underset{|}{\overset{4}{\phantom{X}}}$$
$$\text{Fuc}\alpha\text{1}$$

Given the teachings described herein, it will be evident to those skilled in the art that other saccharides will be suitable within the present invention.

A saccharide may be coupled to a non-saccharide molecule to form a glycoconjugate. For example, a saccharide may be linked to a polyacrylamide. Alternatively, a saccharide may be linked to a lipid. Typical lipids include ceramide, i.e., sphingolipid bases which are acylated on the amine with a fatty acid. For example, sialyl Le$^a$, di-sialyl Le$^a$, or a saccharide cross-reaction with sialyl Le$^a$ and sialyl Le$^x$ may be linked to a ceramide. Alternatively, a saccharide may be bonded to an amino acid or an amino acid-containing molecule, such as a peptide, a polypeptide or a protein. Saccharides are naturally linked to an amino acid or amino acid-containing molecule via the hydroxyl group of a serine or threonine amino acid residue, but can also be linked through other groups such as an amino group.

Saccharides and glycoconjugates provided by the present invention may be represented by structures III and IV as follows:

$$\text{Neu5Ac}\alpha\text{2-3Gal}\beta\text{1-3x}\beta\text{1-3y}\beta\text{1-4z}\beta\text{1-R} \quad (III)$$
$$\underset{|}{\overset{4}{\phantom{X}}}$$
$$\text{Fuc}\alpha\text{1}$$

$$\text{Neu5Ac}\alpha\text{2} \quad (IV)$$
$$\underset{6}{\overset{|}{\phantom{X}}}$$
$$\text{Neu5Ac}\alpha\text{2-3Gal}\beta\text{1-3x}\beta\text{1-3y}\beta\text{1-4z}\beta\text{1-R}$$
$$\underset{|}{\overset{4}{\phantom{X}}}$$
$$\text{Fuc}\alpha\text{1}$$

R includes H, OH, lipid, ceramide, or one or more amino acids; x, y and z are independently selected from saccharides, or either y or z or both may be absent.

Numerous methods for preparing saccharides and glycoconjugates are well known to those skilled in the art. Saccharides may be prepared synthetically using chemical, and/or enzymatic, reagents and techniques. For example, sialyl Le$^a$ saccharides have been prepared by enzymatic synthesis (e.g., Palcic et al., Carbohydr. Res. 190:1–11, 1989). Glycoconjugates may be prepared, for example, through reductive amination. The method of Zopf et al. (Meth. Enzymol. 50:171–175, 1978; Jeffrey et al., Biochem. Biophys. Res. Commun. 62:608–613, 1975) involves 4-aminophenethylamine derivatives of saccharides via reductive amination using sodium borohydride. In brief, sugars are first reacted with the amino reagent by dissolving them in the neat reagent for 15 hours. Sodium borohydride in ethanol is then added. After 5 hours, the product is separated from the reagent by gel filtration and ion exchange chromatography. The derivatives may then be coupled to a molecule containing a group which is reactive with amines. The same amine derivative may be coupled to saccharides using sodium cyanoborohydride. (Svensson et al., J. Immunol. Meth. 25:323–335, 1979). In brief, a sugar is dissolved in water, and the same volume of amine (a 170-fold molar excess) is added together with sodium cyanoborohydride (a ten-fold molar excess). The reduction is performed at pH 8 for 48 hours, and the product purified by gel chromatography. Coupling to different molecules, such as proteins, may be performed by the isothiocyanate coupling method.

Another example of a reagent suitable for preparing glycoconjugates by reductive amination is p-trifluoroacetamidoaniline (TFAN). The reductive amination reaction is carried out in aqueous solution overnight at pH 5–6 with sodium cyanoborohydride as the reducing agent.

Typically, a 5-fold excess of TFAN is used. TFAN-derivatized saccharides are generally protected from oxidation by N-acetylation, e.g., by treatment with methanolic acetic anhydride, to yield TFAc-derivatives. Prior to conjugation, the N-trifluoroacetamido protective group is removed by treatment of the TFAC derivative with aqueous ammonia or 0.5 M sodium hydroxide for 3 hours. Conjugation of the derivatives to molecules, for example to proteins such as bovine serum albumin (BSA), may be achieved by isothiocyanate coupling methods. Other examples of suitable reagents and reactions include p-tetradecylaniline derivatives of saccharides and the preparation of aminoalditols by oxidation of saccharide TFAN derivates with cerium ammonium sulfate (Lindenberg et al., J. Reprod. Fert. 89:431–439, 1990).

The inhibition of the binding of cancer cells expressing sialyl Le$^a$, di-sialyl Le$^a$ or sialyl Le$^x$, to endothelia has a variety of in vitro and in vivo uses. Sialyl Le$^a$ and di-sialyl Le$^a$ are type 1 carbohydrate chains (i.e., have a Galβ1→3GlcNAc polylactosamine unit structure) and sialyl Le$^x$ is a type 2 carbohydrate chain (i.e., has a Galβ1→4 GlcNAc polylactosamine unit structure. A number of cancer cells, such as colorectal and pancreatic, have a prevalence of type 1 carbohydrate chains including sialyl Le$^a$ and di-sialyl Le$^a$. Other cancer cells, such as breast, lung and ovarian, have a prevalence of type 2 carbohydrate chains including sialyl Le$^x$.

Regarding in vitro aspects, as noted above, the present invention provides methods for inhibiting the binding of cancer cells to endothelia in a biological preparation. Representative examples of biological preparations include blood vessel and/or lymph vessel endothelia in combination with a malignancy. The endothelia and the malignancy may be in the form of tissue or cells removed from an organism, or cultured cells. In one embodiment, the method comprises incubating a biological preparation, which contains malignant cells expressing sialyl Le$^a$, di-sialyl Le$^a$ or sialyl Le$^x$ and endothelial cells expressing a LEC-CAM, with an effective amount of at least one agent, such as an antibody, saccharide or glycoconjugate as described above. In another embodiment, the method comprises incubating malignant cells with at least one enzyme inhibitor that inhibits the biosynthesis of sialyl Le$^a$ or di-sialyl Le$^a$ by the cells. Suitable enzyme inhibitors include inhibitors of glycosyltransferases. Representative examples of inhibitors for glycosyltransferases include inhibitors for fucosyltransferases (e.g., as described by Palcic et al., *J. Biol. Chem.* 264:17174–17181, 1989), for N-acetylglucosaminyltransferases (e.g., as described by Palcic et al., *J. Biol. Chem.* 265:6759–6769, 1990), and for sialyltransferases (e.g., as described by Broquet et al., *J. Neurochem.* 54:388–394, 1990; Karaivanova et al., *Cancer Biochem. Biophys.* 11:311–315, 1990).

The present invention also provides methods for inhibiting metastasis in a warm-blooded animal such as a human. In one embodiment, the method comprises administering to a warm-blooded animal an effective amount of at least one agent, such as an antibody, saccharide or glycoconjugate as described above. In another embodiment, the method comprises administering to a warm-blooded animal an effective amount of at least one enzyme inhibitor (as described above) that inhibits the biosynthesis of sialyl Le$^a$ or di-sialyl Le$^a$ by malignant cells. It will be evident to those skilled in the art how to determine the optimal effective dose for a particular agent or enzyme inhibitor, e.g., based upon in vitro and in vivo studies in non-human animals. A variety of routes of administration may be used. Typically, administration will be intravenous, intracavitory (e.g., in pleural or peritoneal cavities), or in the bed of a resected tumor.

An agent may be administered as a composition, i.e., in combination with a pharmaceutically acceptable carrier or diluent, such as physiological saline. It will be recognized by those skilled in the art that an agent and a composition may be prepared in a sterile form. Moreover, an agent may be administered in combination with an immunotherapeutic or chemotherapeutic agent. When such a combination is desired, each substance may be administered sequentially, simultaneously, or combined and administered as a single composition. Diagnostic techniques, such as CAT scans for tumors, may be performed prior to and subsequent to administration to confirm effectiveness.

The following examples are offered by way of illustration and not by way of limitation.

EXAMPLES

Example 1

Glycoconjugates and Assays

Synthetic Glycoproteins (Neoglycoproteins)

Neoglycoproteins were produced by BioCarb AB (Lund, Sweden) by chemically coupling 10–20 moles of a specific oligosaccharide to 1 mole of nonglycosylated albumin, bovine (BSA) or human (HSA). The resulting synthetic glycoprotein (neoglycoprotein) contains multiple copies of the identical carbohydrate sequence, thereby producing a well characterized, mutivalent glycoconjugate which is extremely effective for studying carbohydrate-protein interactions. Depending on the size of the oligosaccharide, three different chemical spacer arms were used to couple the oligosaccharides to proteins 1) p-aminophenyl (PAP); 2) aminophenylethyl (APE); and 3) acetyl phenylene diamine were used to couple the shorter oligosaccharides to albumin since they will retain the anomeric configuration of the reducing sugars which may be involved in a potential binding site. APD was used to couple the larger sugars to protein by reductive amination, which converts the reducing sugar to an aminoaditol.

Direct Binding of Antibodies to Synthetic Glycoproteins (Neoglycoproteins)

Synthetic glycoproteins were coated onto microtiter plates by filling each well with 100 ng of the neoglycoprotein in 100 µl of 0.15 M sodium chloride, 0.01 M sodium phosphate, 0.1% sodium azide, pH 7.4, (PBS-azide) overnight at 4° C. Standard enzyme-linked immunoassays (ELISA) were then performed on the solid phase carbohydrate structures using the appropriate antibody diluted to 10 µ/ml.

Production of ELAM-1 cDNA Transfected Cell Lines

L1-2/pMRB107 cells (L1-2$^{ELAM-1}$) were prepared by transfecting the ELAM-1 gene into the murine pre-B cell line L1-2 (Gallatin et al., *Nature* 304:30–34, 1983). A cDNA clone encoding ELAM-1 was obtained from a cDNA library made from activated human umbilical vein endothelial cell cultures by polymerase chain reaction (PCR) amplification. The ELAM-1 gene was inserted downstream of the hCMV promoter in pMRB101 [a derivative of EE6 which contains the *E. coli* gpt gene (Mulligan and erg, *Proc. Nat'l. Acad. Sci. USA* 78:2072, 1981; Stephens and Corbett, *N.A.R.* 17:7110, 1989)]. DNA was introduced into L1-2 cells by electroporation and the cells selected for resistance to mycophenolic acid. A population of cells staining brightly for ELAM-1 were selected by FACS and cloned by limiting dilution. These cells are ELAM-1$^{hi}$ LFA-1$^{mod}$ CD45$^{hi}$ CD44$^{neg}$ LECAM-1$^{neg}$, differing from the parent cell line or control vector transfectants only in their expression of ELAM-1. L1-2/pMRB101 (L1-2$^{vector}$) cells are a similarly transformed derivative of L1-2 transfected with pMRB101 and lacking ELAM-1 expression.

Cell Binding Assays

One hundred microliter samples of each synthetic glycoconjugate in phosphate buffered saline (PBS), pH 7.2, were absorbed onto glass wells of 8-chamber slides (LabTek) for two hours at RT. For some experiments glass slides were pre-coated with rabbit anti-human serum albumin (Sigma) at 200 µg/ml overnight at 4° C. and washed with PBS prior to the addition of the glycoconjugate. After blocking with 5% NBS/10 mM HEPES/Dulbecco's Modified Eagles Medium (DMEM), pH 7.0 (CM), L1-2$^{ELAM-1}$ or L1-2$^{vector}$ cells were applied to each well (1.5×10$^6$/0.15 ml in CM). After a 25 minute incubation at RT on a rotating shaker at 50 rpm, the tops of the wells were removed and the slides washed 3× in DMEM and then fixed by incubation in 1.5% glutaraldehyde (Kodak)/DMEM. Three to six 100× fields were counted for each data point.

Inhibition of Binding of ELAM-1 Containing Cells by Compounds

One hundred and twenty nanograms of Sialyl Le$^a$-HSA or Sialyl Le$^x$-HSA dissolved in 100 μl of phosphate-buffered saline were absorbed per well of an 8 chambered glass (LabTek) slide for 2 hours at room temperature. During this period, L1-2$^{ELAM-1}$ cells were pre-incubated for 20 minutes on ice with increasing concentrations of Sialyl Le$^a$-HSA at 10$^7$ cells/ml. After washing and blocking the wells in Complete Medium (CM, 5% normal bovine serum, 10 mM HEPES, pH 7.0, DMEM), L1-2$^{ELAM-1}$ cells pre-incubated with compounds were added (1×107 cells/ml) and incubated at room temperature while rotating at 50 rpm. After 25 minutes, slides were washed 3 times in Dulbecco's Modified Eagles Medium (DMEM) and then fixed in 1.5% glutaraldehyde/DMEM.

Example 2

Carbohydrate Structure Recognized by ELAM-1

The sensitive binding assay described in Example 1 uses cells permanently transfected with ELAM-1 cDNA. The mouse pre-B cell line, L1-2, transfected with ELAM-1 cDNA (L1-2$^{ELAM-1}$), but not vector control cDNA, L1-2$^{vector}$ expresses very high levels of ELAM-1. The ELAM-1 expressed by these cells is functional as L1-2$^{ELAM-1}$ cells are adhesive for neutrophils and this adhesion is blocked by anti-ELAM-1 monoclonal antibodies. When added to glass slides coated with various synthetic glycoconjugates, L1-2$^{ELAM-1}$ cells bound selectively to Sialyl Le$^a$ and Sialyl Le$^x$ neoglycoproteins, but not to a number of other glycoconjugates. L1-2$^{ELAM-1}$ cells also bound, albeit more weakly, to Le$^a$ neoglycoprotein. The binding to Le$^a$ is significant as L1-2$^{ELAM-1}$ cells bound poorly to Le$^x$ and not at all to the glycoconjugates prepared with the structural analogs such as LNF I. That L1-2$^{ELAM-1}$ cells did not bind other monosialylated carbohydrates, such as 3'SL, 6'SL, LSTa or LSTc demonstrates that the binding to Sialyl Le$^a$ and Sialyl Le$^x$ is not due to non-specific charge effects, but rather reflects specific structural features of these oligosaccharides. The low level of binding of ELAM-1 transfectants to Le$^a$ is consistent with an essential role of fucose in recognition, but shows that neuraminic acid (also known as sialic acid) also plays a key role.

All publications and patent applications mentioned in this specification are herein incorporated by reference to the same extent as if each individual publication or patent application was specifically and individually indicated to be incorporated by reference.

From the foregoing, it will be evident that, although specific embodiments of the invention have been described herein for purposes of illustration, various modification may be made without deviating from the spirit and scope of the invention.

What is claimed is:

1. A method for inhibiting in a warm-blooded animal the spread of malignant cells expressing sialyl Le$^a$ or di-sialyl Le$^a$, to secondary sites, comprising:

administering to a warm-blooded animal an effective amount of at least one agent that inhibits the binding of malignant cells expressing sialyl Le$^a$ or di-sialyl Le$^a$, to endothelial cells expressing a LEC-CAM, wherein said agent is selected from the group consisting of sialyl Le$^a$, a carbohydrate portion of sialyl Le$^a$, di-sialyl Le$^a$, a carbohydrate portion of di-sialyl Le$^a$, and a glycoconjugate that includes a carbohydrate portion of sialyl Le$^a$ or di-sialyl Le$^a$ or derivative of either that inhibits the binding of sialyl Le$^a$ or di-sialyl Le$^a$ to a LEC-CAM.

2. The method of claim 1 wherein the agent is said glycoconjugate.

3. A method for inhibiting in a warm-blooded animal the spread of malignant cells expressing sialyl Le$^a$ or di-sialyl Le$^a$, to secondary sites by hematogenous metastases, comprising:

administering to a warm-blooded animal an effective amount of at least one agent that inhibits the binding of malignant cells expressing sialyl Le$^a$ or di-sialyl Le$^a$, to endothelial cells expressing ELAM-1, wherein said agent is selected from the group consisting of sialyl Le$^a$, a carbohydrate portion of sialyl Le$^a$, di-sialyl Le$^a$, a carbohydrate portion of di-sialyl Le$^a$, and a glycoconjugate that includes a carbohydrate portion of sialyl Le$^a$ or di-sialyl Le$^a$ or derivative of either that inhibits the binding of sialyl Le$^a$ or di-sialyl Le$^a$ to ELAM-1.

4. The method of claim 3 wherein the agent is said glycoconjugate.

* * * * *